US010973267B1

(12) United States Patent
Correa et al.

(10) Patent No.: US 10,973,267 B1
(45) Date of Patent: Apr. 13, 2021

(54) PERSONAL PROTECTIVE AND MONITORING DEVICE

(71) Applicant: RECIPROTECT LLC, Ocean City, MD (US)

(72) Inventors: Rafael S Correa, Berlin, MD (US); Rafael A. Correa, Berlin, MD (US)

(73) Assignee: Reciprotect LLC, Ocean City, MD (US)

( * ) Notice: Subject to any disclaimer, the term of this patent is extended or adjusted under 35 U.S.C. 154(b) by 0 days.

(21) Appl. No.: 16/922,084

(22) Filed: Jul. 7, 2020

Related U.S. Application Data

(60) Provisional application No. 63/010,863, filed on Apr. 16, 2020.

(51) Int. Cl.
| | | |
|---|---|---|
| *A41D 13/11* | (2006.01) | |
| *A42B 3/22* | (2006.01) | |
| *A61B 5/01* | (2006.01) | |
| *A61F 9/04* | (2006.01) | |

(52) U.S. Cl.
CPC ............ *A41D 13/1184* (2013.01); *A61B 5/01* (2013.01); *A61F 9/045* (2013.01); *A42B 3/225* (2013.01)

(58) Field of Classification Search
CPC ........ A41D 13/1185; A61B 8/01; A61F 9/045
USPC .............................................................. 2/9
See application file for complete search history.

(56) References Cited

U.S. PATENT DOCUMENTS

| | | | | |
|---|---|---|---|---|
| 3,704,625 A | * | 12/1972 | Seto | ...................... G01K 11/165 |
| | | | | 374/162 |
| 4,875,477 A | | 10/1989 | Waschke et al. | |
| 4,986,282 A | * | 1/1991 | Stackhouse | ............... A61F 9/02 |
| | | | | 128/857 |
| 5,086,515 A | * | 2/1992 | Giuliano | ................... A61F 9/06 |
| | | | | 2/8.1 |
| 5,182,816 A | * | 2/1993 | Arai | ...................... A42B 3/222 |
| | | | | 2/424 |
| 7,490,359 B2 | * | 2/2009 | Landis | ............... A41D 13/1184 |
| | | | | 2/9 |
| 2009/0255535 A1 | | 10/2009 | Kanzer | |
| 2011/0024323 A1 | | 2/2011 | Martorano et al. | |
| 2012/0084904 A1 | * | 4/2012 | Paulson | ................. A42B 3/225 |
| | | | | 2/422 |
| 2016/0015098 A1 | | 1/2016 | Conlon | |
| 2016/0199674 A1 | * | 7/2016 | Johnson | ............... A43B 1/0081 |
| | | | | 600/549 |
| 2017/0361132 A1 | * | 12/2017 | Dykes | .................... G01C 21/16 |
| 2019/0125011 A1 | | 5/2019 | Eisenbrey et al. | |

* cited by examiner

*Primary Examiner* — Gloria M Hale
(74) *Attorney, Agent, or Firm* — Laubscher & Laubscher, P.C.

(57) ABSTRACT

A protective face guard apparatus includes a transparent shield, head strap and temperature measuring mechanism. The shield has top, side and bottom edges, and the head strap is connected with the shield. Preferably, the shield has an arcuate configuration. The temperature measuring mechanism includes a temperature indicator that is connected with the shield or head strap such that when the face guard is worn on the head of an individual and the temperature measuring mechanism measures a temperature of the individual, the indicator displays an indication of the temperature. Preferably, the head strap includes a flexible portion having a generally semicircular or circular configuration.

13 Claims, 3 Drawing Sheets

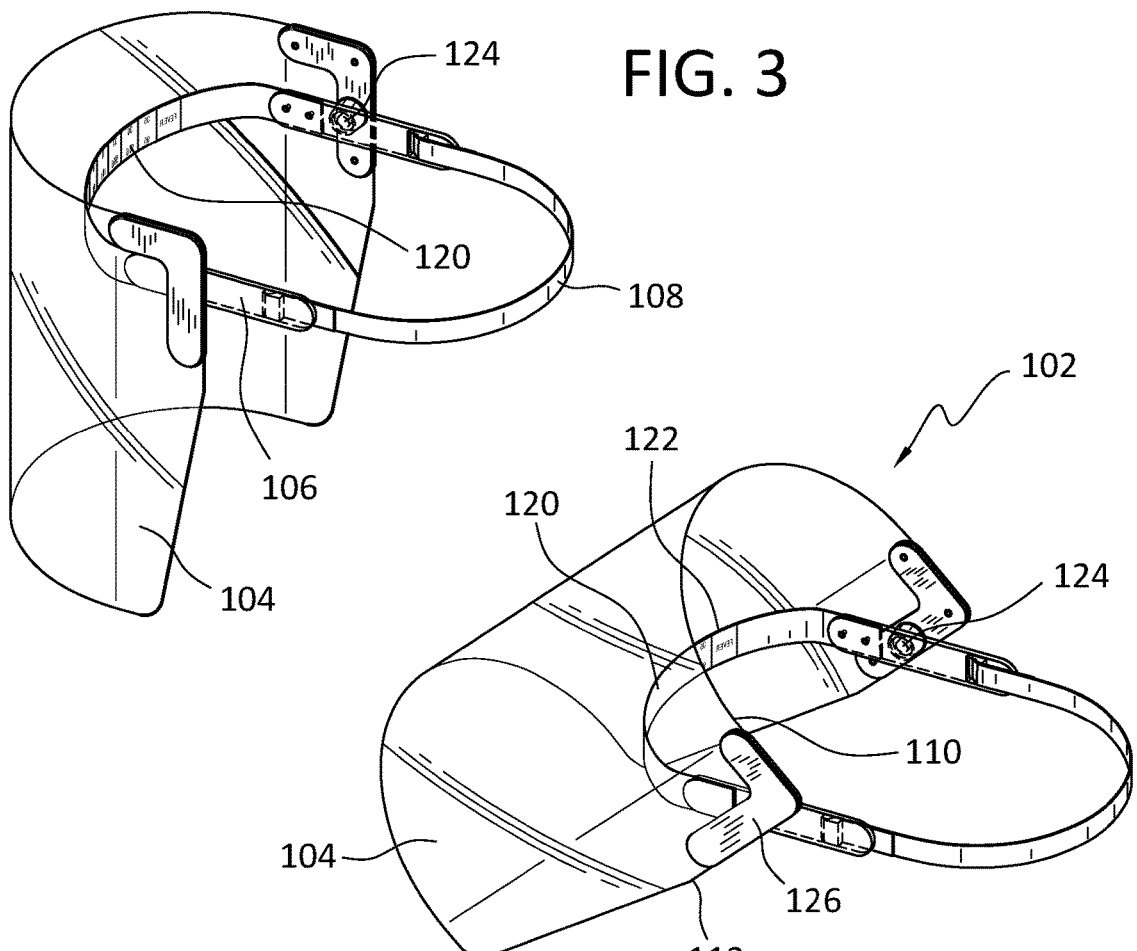
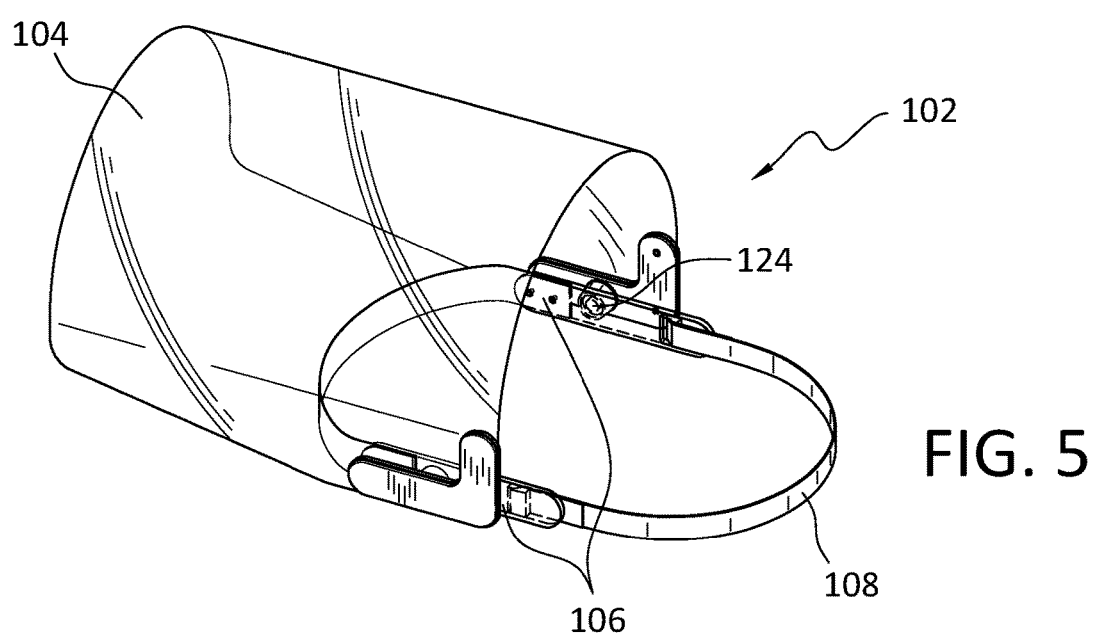

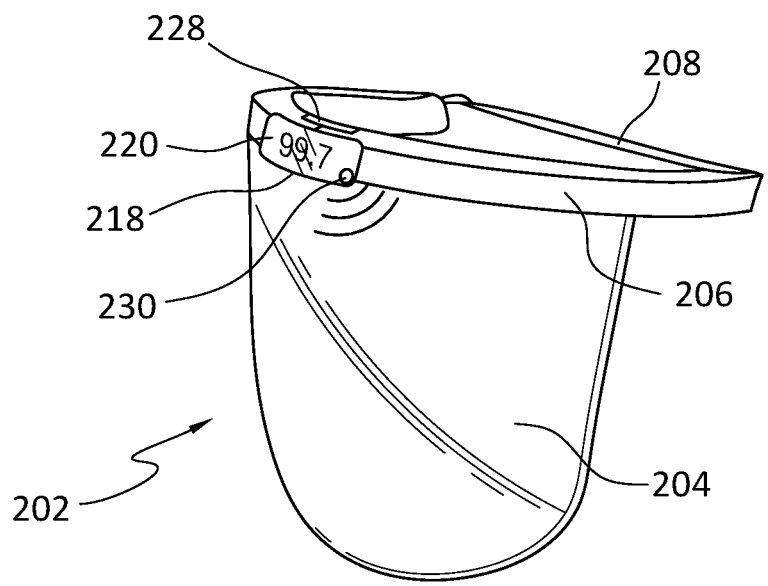
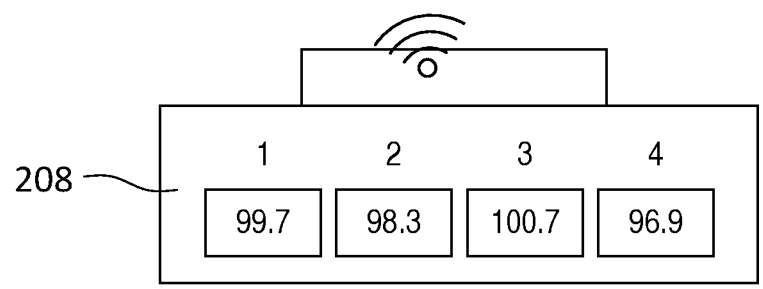
FIG. 6
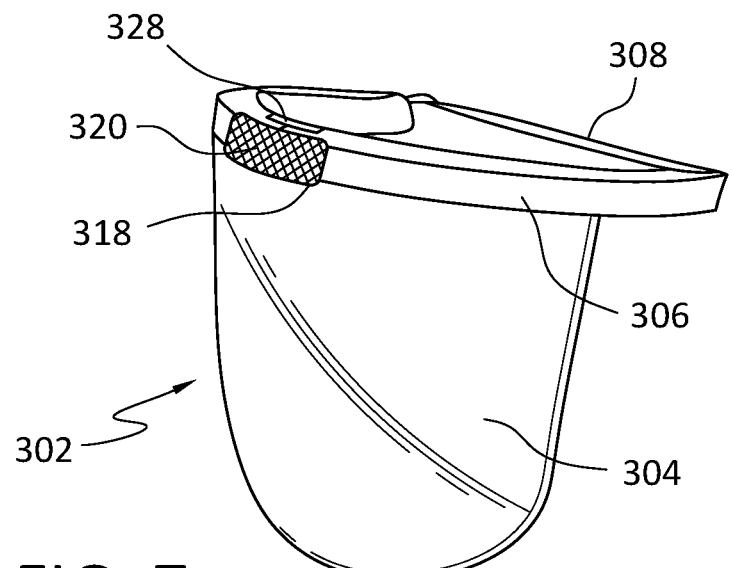
FIG. 7

PERSONAL PROTECTIVE AND MONITORING DEVICE

This application claims the benefit of U.S. provisional patent application No. 63/010,862 filed Apr. 16, 2020.

BACKGROUND OF THE DISCLOSURE

The present disclosure relates generally to a personal protective device such as a faceguard, and more specifically to a transparent faceguard having a temperature indicator.

Protective faceguards or shields are known in the art. They are used in certain professional settings, such as in laboratories and hospitals, to protect the face of an individual from harmful materials and/or bacteria. Such faceguards preferably include a transparent shield which protects the individual but does not obstruct the individual's view.

Though such protective faceguards provide beneficial protections to the individual wearing the shield, and they are used by many in certain hazardous professions, known faceguards provide nothing more than protection. Thus there is an opportunity to improve faceguards currently used in many fields such that they provide additional benefits over those currently in use.

BRIEF DESCRIPTION OF THE PRIOR ART

One example of a faceguard that provides features beyond protecting an individual's face is a temperature sensitive surgical face mask disclosed in the Eisenbrey et al. Patent Application Publication No. 2019/0125011. The face mask includes a material which changes the partial or entire color of the face mask or a portion of the face mask to indicate that the mask wearer has an active fever. The masks disclosed in Eisenbrey include a cloth mask that has a thermochromatic material incorporated therein at the time of manufacture or applied to a previously manufactured mask. The preferred materials include leuco dyes, liquid crystal materials, or thermochromatic paints.

Though face masks such as those disclosed in Eisenbrey have their benefits and improve on known face masks in the art, they also have their drawbacks. For instance, the Eisenbrey face mask applies to fabric-based face masks to which the thermochromatic material is applied. It does not provide a solution for face masks made of a transparent rigid material such as plastic. Such masks cannot include the thermochromatic material as currently constructed without the addition of another material to the mask.

Accordingly, there is a need for a protective faceguard in the form of a transparent face shield that includes features beyond protection.

SUMMARY OF THE DISCLOSURE

Accordingly, it is an object of the present disclosure to provide a protective face guard that includes a transparent shield, head strap, and a temperature measuring mechanism. The shield has top, side and bottom edges, and the head strap is connected with the shield adjacent to the top and side edges. Preferably, the shield has an arcuate configuration. The temperature measuring mechanism includes a temperature indicator that is connected with the shield or head strap such that when the face guard is worn on the head of an individual, the temperature measuring mechanism measures a temperature of the individual and the indicator displays an indication of the individual's temperature. Preferably, the head strap includes a flexible portion and has a generally semicircular or circular configuration.

In one embodiment, the face guard further includes a ratcheting device for rotating the shield and the temperature indicator includes a graduated scale, such as a numerical temperature strip or a spectrum of colors.

In another embodiment, the temperature indicator includes a specific numerical temperature or range of temperature. Preferably, the temperature is digitally displayed.

In yet another embodiment, the temperature indicator includes at least one color which is activated and displayed based on the measured temperature.

BRIEF DESCRIPTION OF THE FIGURES

Other objects and advantages of the disclosure will become apparent from a study of the following specification when viewed in the light of the accompanying drawing, in which:

FIGS. 2-5 are perspective views of a second embodiment of a face guard according to the present disclosure;

FIG. 6 is a perspective view of a third embodiment of a face guard according to the present disclosure; and FIG. 7 is a perspective view of a fourth embodiment of a face guard according to the present disclosure.

DETAILED DESCRIPTION

Figure 1:
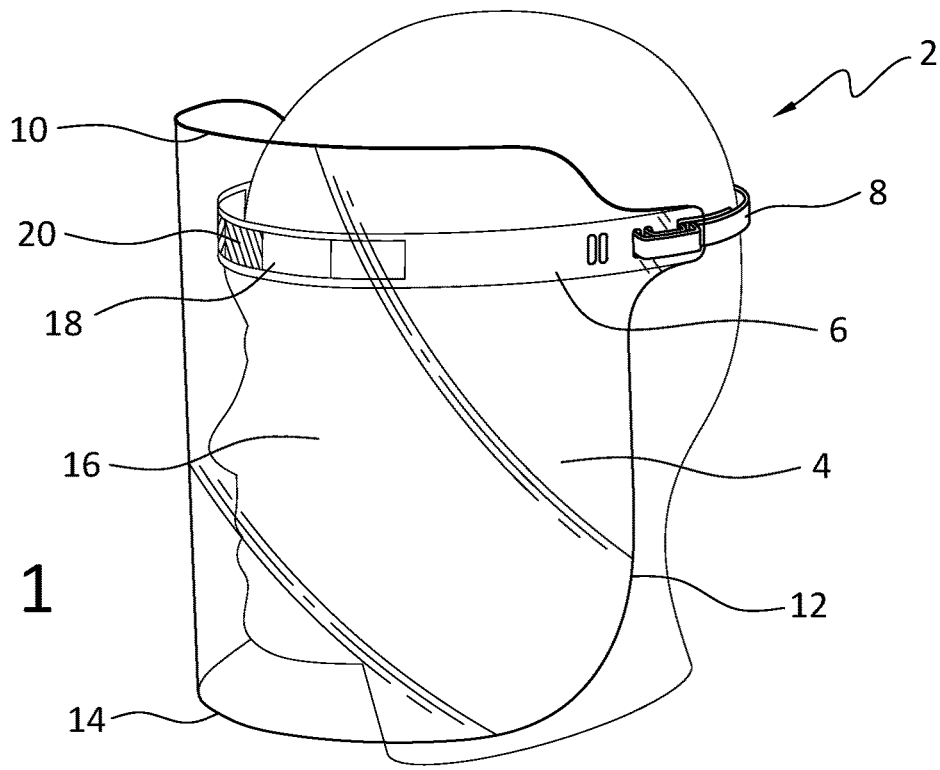
FIG. 1 is a perspective view of a first embodiment of a face guard being worn on an individual's head according to the present disclosure.
Figure 2:
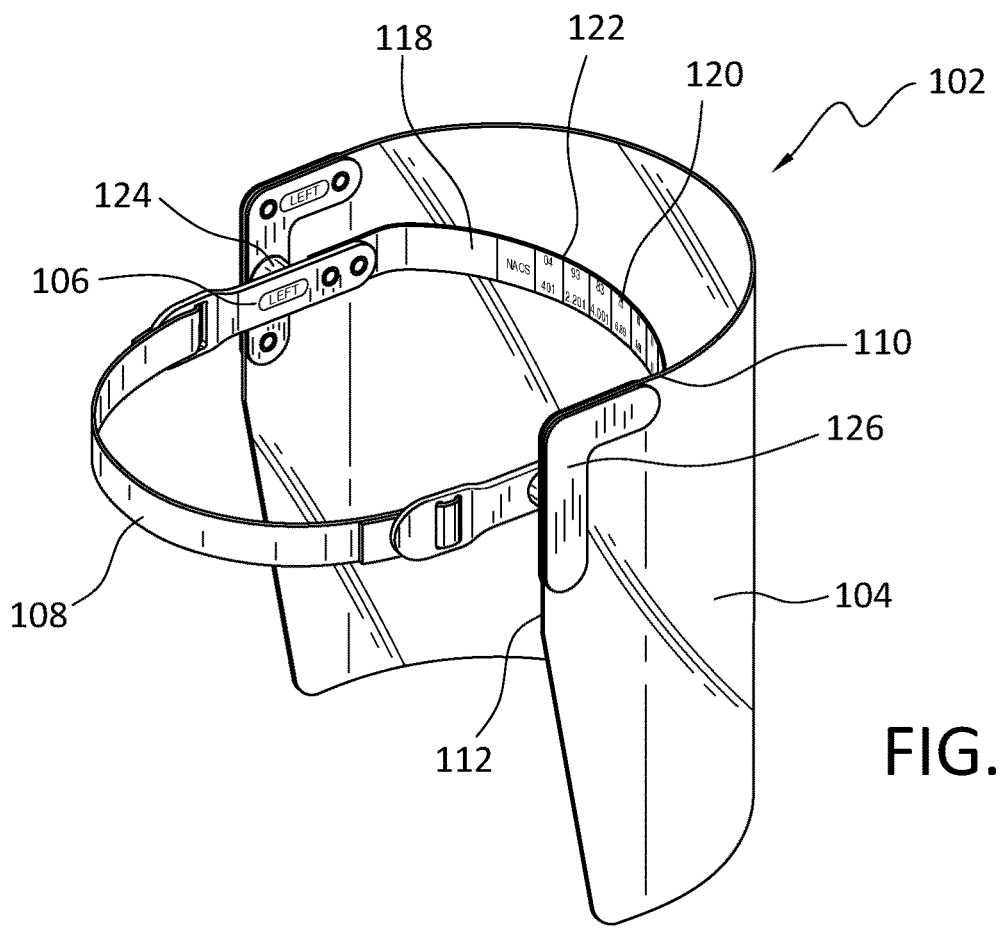

The present disclosure relates to a face guard with a shield and temperature measuring device. Referring first to FIG. 1, there is shown a first embodiment of the protective face guard apparatus 2 being worn on the head of an individual. The apparatus includes a transparent shield 4 connected with a frame 6 and head strap 8. The shield has top 10, side 12 and bottom 14 edges and covers the entirety of the individual's face 16. The frame is connected with the shield near its upper edge. It contacts the individual's forehead to provide stability and to secure the shield in place.

Connected with the frame is a thermosensitive device 18 which includes a temperature indicator 20, similar to that of paper, disposable thermosensitive strips known in the art. The device of FIG. 1 includes a plastic strap with a material that reacts to specific temperatures, such as a heat sensitive liquid crystal. The strap includes six temperature ranges of heat crystals, each of which reacts to a different temperature. For instance, if the strip is placed on an individual's head, which is accomplished by wearing the face guard, and the individual has a temperature below 95 degrees Fahrenheit, one section of heat-sensitive crystals will react, resulting in that of the temperature strip changing color. Beyond that, if an individual's temperature is approximately 95°-97°, a second section will change color, 97°-99°, a third section will change color, 99°-101° a fourth, 101°-103° a fifth, and for any temperature above 103°, all six regions will change color. The change in color is easily visible to an observer, indicating the body temperature of the individual to which the strip is applied. Further, each region includes a different color from the other regions, which makes it easy for an observer to know the number of regions that have been activated. It will be understood by those with skill in the art that different numbers of temperature ranges than those disclosed above could be used with the device.

The strip 18 is connected with the frame 6 and arranged such that an inner surface of the strip contacts the forehead of an individual when the individual straps the frame to his or her head. The outer surface of the strip is visible through the transparent shield 4, and anyone in proximity to the individual wearing the face guard is able to observe which if any portions of the strip have changed color. As noted above, if the temperature of the individual meets the temperature threshold of a liquid crystal, the portion of the strip with that liquid crystal changes color to indicate the temperature of the individual has met or surpassed the threshold. The strip could include different threshold temperature ranges from those noted above, and, as detailed below, different methods and devices for measuring and displaying an individual's temperature can be used.

Referring now to FIGS. 2-5, there is shown a protective face guard apparatus 102 that includes a graduated temperature device 118 having a temperature indicator 120. This embodiment also includes a transparent shield 104, frame 106 and strap 108. There is space between the shield and front 122 of the frame to allow for the free flow of air. Without that opening, heat can become trapped between the shield and frame which would potentially cause false temperature readings, a fogged shield and/or discomfort. When the face guard is worn by an individual, the inner surface of the temperature strip contacts the forehead of the individual and measures the individual's temperature. Based on the temperature, crystals of the strip are activated and the strip changes color to indicate the specific temperature of the individual. As with the embodiment in FIG. 1, the strip includes heat-sensitive liquid crystals that change color based on temperature thresholds. However, in this instance, rather than simply changing colors, the strip includes a range of numerical temperatures. Thus, an observer can determine the approximate numerical temperature of an individual based on which portion of the strip has changed color. And if the strip reaches 101°+ Fahrenheit, the observer will know that the individual wearing the face guard has a fever.

The shield 104 and frame 106 shown in FIGS. 2-5 are connected via a ratcheting device 124 which allows for the shield to rotate between a closed position (FIG. 3), which covers the face of an individual, to an open position (FIG. 5), which exposes the face of an individual and, to any number of positions in between. The ratcheting device includes a base 126 that has an L-shaped configuration for connecting the device along the interface between the top 110 and side 112 edges of the shield. It will be understood by those with skill in the art that, rather than a ratcheting device, other device that allow for the mask to rotate between an open and closed position could be used without deviating from the purpose of the ratcheting device.

FIG. 6 shows a face guard 202 that also includes a transparent face shield 204 connected with a frame 206 including a strap 208. However, rather than having a temperature strip, the temperature mechanism 218 in this embodiment includes a digital display 220 showing the specific temperature of the individual wearing the face guard. The temperature measuring mechanism also includes a sensor 228 which contacts the head of an individual when the individual is wearing the face guard. The sensor is connected with the digital display 220 which displays a specific numerical temperature, in this case 99.7°. The display can be observed by anyone in proximity with the individual wearing the face guard.

The temperature mechanism of the face guard of FIG. 6 includes a radio wave device 230, such as a Bluetooth device, that connects with a remote monitor 232. The monitor can be connected with one or more face guards to monitor the temperature of one or more individuals. As is shown in FIG. 6, the monitor is connected with four face shields, three of which are not shown.

FIG. 7 shows a face guard 302 that is similar to that of FIG. 3 in that it includes a transparent shield 304, frame 306, strap 308, and temperature measuring device 318, but the indicator 320 of the temperature measuring device includes a light-emitting diode (LED) rather than a digital temperature display. The LED is connected with a sensor 328 which contacts the forehead of the individual wearing the face guard and measures his or her temperature. A signal is sent to the LED display to power a specific color, for instance a green, yellow or red light may be included to indicate a normal temperature, slightly elevated temperature, or fever, respectively. Alternatively, the LED may include only a single color which is switched on only when a temperature threshold that indicates a fever is met. As with the other embodiments, individuals in close proximity to the person wearing the face guard can observe if the LED is switched on and in turn whether the individual has an elevated temperature.

Although the above description references particular embodiments, it is to be understood that these embodiments are merely illustrative of the principles and applications of the present disclosure. It is therefore to be understood that numerous modifications may be made to the illustrative embodiments and that other arrangements may be devised and employed without departing from the spirit and scope of the present disclosure.

What is claimed is:

1. A protective face guard apparatus, comprising:
 a. a transparent shield having a top edge, a bottom edge, and a pair of side edges;
 b. a head strap assembly connected with said shield, including:
  i. a pair of head strap frames each connected in parallel spaced relation with one of said side edges, respectively;
  ii. a strap connected with said head strap frames; and
  iii. a flexible temperature measuring strip including a temperature indicator configured for contact with the forehead of an individual and connected with one of said strap and said pair of head strap frames, whereby when the face guard apparatus is worn on the head of an individual, said flexible temperature measuring strip contacts the forehead of the individual to measure a temperature of the individual and display an indication of the measured temperature on said strip.

2. A protective face guard apparatus as defined in claim 1, and further comprising a ratcheting device connected with said head strap assembly and said transparent shield to provide rotation of said shield from a first closed position to a second open position and to any position therebetween.

3. A protective face guard apparatus as defined in claim 2, wherein said ratcheting device includes a base having an L-shaped configuration connected with said shield at an interface between said top and side edges.

4. A protective face guard apparatus as defined in claim 1, wherein said temperature measuring strip includes a range of numerical temperatures.

5. A protective face guard apparatus as defined in claim 1, wherein said temperature measuring strip includes a graduated spectrum.

6. A protective face guard apparatus as defined in claim 1, wherein said temperature measuring strip displays a numerical temperature.

7. A protective face guard apparatus as defined in claim 5, wherein said temperature measuring strip includes at least one color.

8. A protective face guard apparatus as defined in claim 1, wherein said head strap assembly is flexible and has a generally circular configuration.

9. A protective face guard apparatus as defined in claim 1, wherein said transparent shield has an arcuate configuration in a horizontal cross section.

10. A protective face guard apparatus as defined in claim 1, wherein said strap includes a front strap portion and a rear strap portion each connected with said pair of head strap frames, said front strap portion including said flexible temperature measuring strip and configured for contact with the forehead of a user, said rear strap portion configured for contact with the back of the head of a user.

11. A protective face guard apparatus as defined in claim 1, wherein said face guard shield is open at an upper end.

12. A protective face guard apparatus as defined in claim 6, wherein said temperature measuring strip comprises a heat sensitive liquid crystal thermometer.

13. A protective face guard apparatus, comprising:
 a. a transparent shield having a top edge, a bottom edge, and a pair of side edges;
 b. a head strap assembly connected with said shield, including:
  i. a pair of head strap frames each connected in parallel spaced relation with one of said side edges, respectively;
  ii. a strap connected with said head strap frames; and
  iii. a flexible temperature measuring strip including a temperature indicator configured for contact with the forehead of an individual and connected with said pair of head strap frames, whereby when the face guard apparatus is worn on the head of an individual, said flexible temperature measuring strip contacts the forehead of the individual to measure a temperature of the individual and display an indication of the measured temperature on said strip.

\* \* \* \* \*